(12) United States Patent
Hatori

(10) Patent No.: US 7,633,623 B2
(45) Date of Patent: Dec. 15, 2009

(54) OPTICAL TOMOGRAPHY SYSTEM

(75) Inventor: Masami Hatori, Kanagawa-ken (JP)

(73) Assignee: FUJIFILM Corporation, Tokyo (JP)

(*) Notice: Subject to any disclaimer, the term of this patent is extended or adjusted under 35 U.S.C. 154(b) by 276 days.

(21) Appl. No.: 11/529,436

(22) Filed: Sep. 29, 2006

(65) Prior Publication Data
US 2007/0086012 A1 Apr. 19, 2007

(30) Foreign Application Priority Data
Sep. 30, 2005 (JP) ............................ 2005-289116

(51) Int. Cl.
*G01B 9/02* (2006.01)
(52) U.S. Cl. .................... 356/450; 356/479; 356/511
(58) Field of Classification Search ................ 356/497, 356/479, 450, 511
See application file for complete search history.

(56) References Cited

U.S. PATENT DOCUMENTS 6,191,862 B1 * 2/2001 Swanson et al. ............ 356/479
7,133,138 B2 * 11/2006 Horii et al. ................. 356/497
7,180,600 B2 * 2/2007 Horii et al. ................. 356/479
7,450,242 B2 * 11/2008 Toida et al. ................. 356/479
2006/0215170 A1 * 9/2006 Toida et al. ................. 356/479
2006/0256348 A1 * 11/2006 Toida et al. ................. 356/511
2007/0086011 A1 * 4/2007 Toida ......................... 356/450

FOREIGN PATENT DOCUMENTS

| JP | 6-165784 A | 6/1994 |
| JP | 2003-139688 | 5/2003 |

* cited by examiner

*Primary Examiner*—Kiet T Nguyen
(74) *Attorney, Agent, or Firm*—Sughrue Mion, PLLC

(57) ABSTRACT

Light emitted from the light source unit is divided into measuring light and reference light. An optical path length of the measuring light or the reference light which has been divided by the light dividing means is adjusted. Interference light of the reflected light and the reference light is detected and a tomographic image of the object is obtained on the basis of the detected interference light. The optical path length is adjusted by a reflecting mirror which reflects the measuring light or the reference light radiated from the optical fiber, a first lens which is disposed between the reflecting mirror and the optical fiber and a second lens which collects the measuring light or the reference light made parallel by the first lens on the reflecting mirror and makes parallel the measuring light or the reference light reflected by the reflecting mirror.

13 Claims, 7 Drawing Sheets

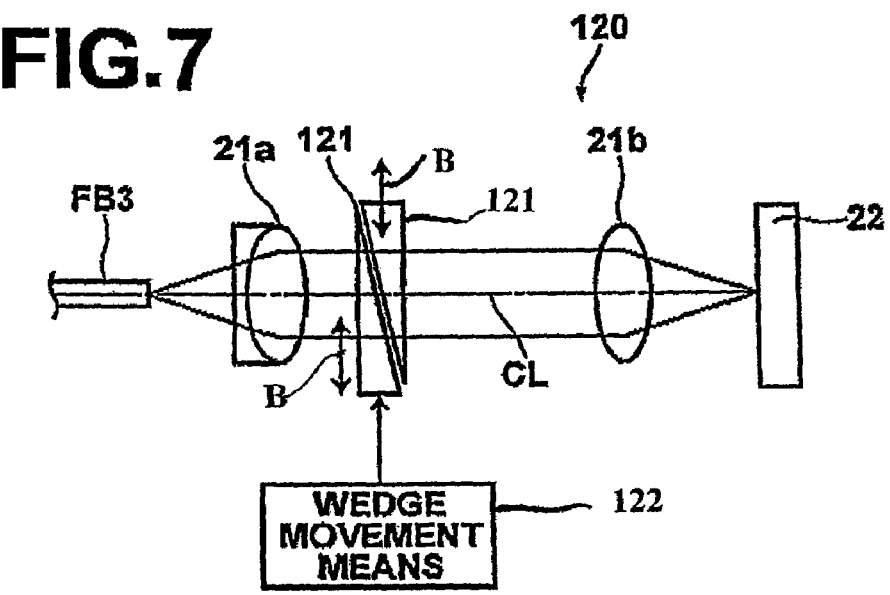
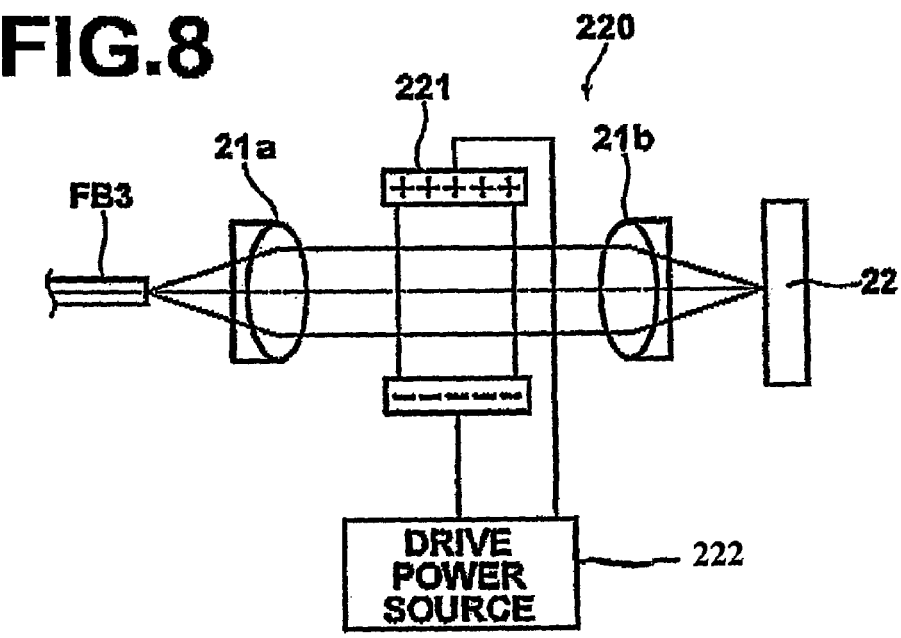

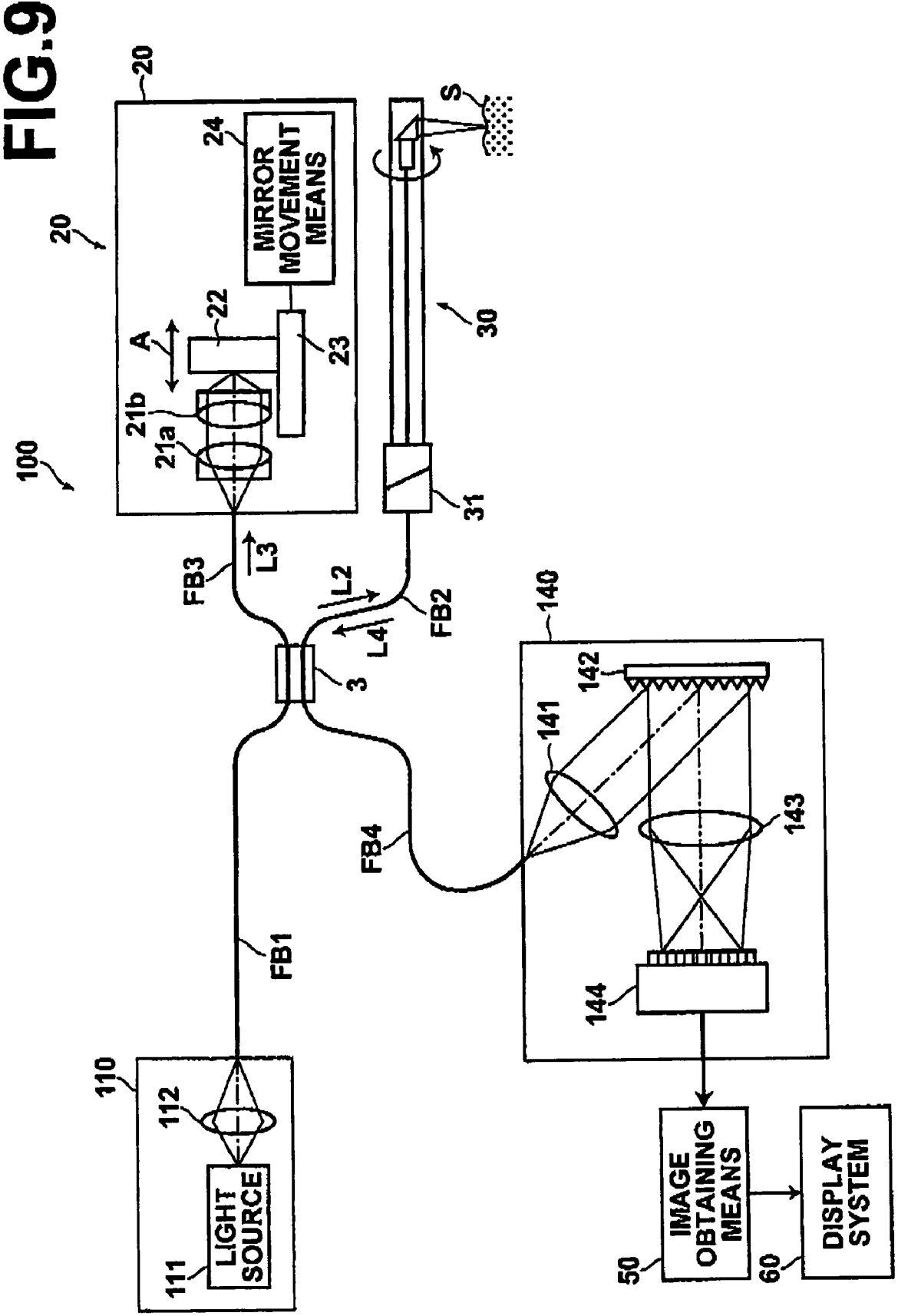

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

As a method of obtaining a tomographic image of an object of measurement such as living tissue, there has been proposed, in addition to an ultrasonic tomography system, a method where OCT (optical coherence tomography) is measured as disclosed in Japanese Unexamined Patent Publication Nos. 6(1994)-165784 and 2003-139688. In the OCT measurement, a phenomenon that interference light is detected when the optical paths of the measuring light and the reflected light conform to the optical path of the reference light in length is used. That is, in this method, low coherence light emitted from a light source is divided into measuring light and reference light and the measuring light is projected onto the object of measurement, while the reflected light from the object of measurement is led to a mixing means. The reference light is led to the mixing means after its optical path length is changed in order to change the depth of measurement in the object. By the mixing means, the reflected light and the reference light are superposed one on another, and interference light due to the superposition is detected by, for instance, heterodyne detection.

In the above OCT system, a tomographic image is obtained by sweeping the optical path length of the reference light, thereby changing the measuring position (the depth of measurement) in the object. This technique is generally referred to as "TD-OCT (time domain OCT)". More specifically, in the optical path length changing mechanism for the reference light disclosed in Japanese Unexamined Patent Publication No. 6(1994)-165784, an optical system which collects the reference light emitted from the optical fiber on a mirror is provided and the optical path length is adjusted by moving only the mirror in the direction of the beam axis of the reference light. Further, in the optical path length changing mechanism for the reference light disclosed in Japanese Unexamined Patent Publication No. 2003-139688, the reference light emitted from the optical fiber is turned to parallel light by a parallel lens, and the reference light in the parallel light is collected and caused to enter the optical fiber again by an optical path length adjusting lens, and the optical path length adjusting lens is moved back and forth in the direction of the beam axis of the reference light to adjust the optical path length.

Whereas, as a system for rapidly obtaining a tomographic image without changing the optical path length of the reference light, there has been proposed an SS-OCT (swept source OCT) system where interference light is detected while the frequency of the light emitted from the light source is changed with time. In the SS-OCT system, an interferogram interference intensity signal is obtained without changing the optical path length by sweeping the frequency of the laser beam emitted from the light source to cause the reflected light and the reference light to interfere with each other by the use of a Michelson interferometer. Then a tomographic image is generated by carrying out a Fourier analysis on the interferogram signal in the region of an optical frequency.

Whereas, as a system for rapidly obtaining a tomographic image without sweeping the optical path length of the reference light, there has been proposed an optical tomography method of obtaining an optical tomographic image by measurement of SD-OCT (spectral domain OCT). In the SD-OCT system, a tomographic image is formed without scanning in the direction of depth, by dividing broad band, low coherence light into measuring light and reference light by the use of a Michelson interferometer, and carrying out a Fourier analysis on each channeled spectrum obtained by decomposing the interference light of the reflected light, which returns when projecting the measuring light onto the object, and the reference light into frequency components.

In the SD-OCT system and the SS-OCT system described above, it is still necessary to adjust the optical path difference within an interference distance within which the measuring light and the reference light can interfere with each other, that is, to adjust the optical path length of the reference light (or the measuring light) within a measurable range within which a tomographic image can be obtained. As a means for adjusting the optical path length, it is conceivable to employ the optical path length adjusting mechanism disclosed in Japanese Unexamined Patent Publication Nos. 6(1994)-165784 and 2003-139688.

However, when only a mirror or a lens is moved as in the optical path length adjusting mechanism disclosed in Japanese Unexamined Patent Publication No. 6(1994)-165784, there is involved a problem that a stable intensity of the reflected light cannot be obtained when the measuring position is scanned in the direction of depth since light radiated from the optical fiber cannot be collected on the mirror and reflected light from the mirror which enters the optical fiber is reduced in amount.

Further, when an optical path length adjusting lens is moved back and forth in the direction of the optical axis of the reference light in order to adjust the optical path length, the position of focus of the optical path length adjusting lens is also moved and there is involved a problem that a stable intensity of the interference light cannot be obtained when the measuring position is scanned in the direction of depth since reference light radiated from the optical path changing lens which enters the optical fiber is reduced in amount.

That is, when reference light propagating an optical fiber is taken out to be adjusted in its optical path length and is returned to the optical fiber, it is necessary to cause the light to enter the core of the optical fiber which is several μm to ten μm in its diameter. Accordingly, a stable intensity of the interference light cannot be obtained and the quality of the image can deteriorate when the measuring position is scanned in the direction of depth since the amount of reference light which enters the optical fiber when light is deviated from the core of the optical fiber or the beam diameter is increased upon adjustment of the optical path length disclosed in Japanese Unexamined Patent Publication Nos. 6(1994)-165784 and 2003-139688.

Also when the optical path length adjusting mechanisms disclosed in Japanese Unexamined Patent Publication Nos. 6(1994)-165784 and 2003-139688 are employed in the SS-OCT system and the SD-OCT system, there is a problem that the intensity of interference light is reduced upon adjustment of the optical path length and the quality of the image can deteriorate.

SUMMARY OF THE INVENTION

In view of the foregoing observations and description, the primary object of the present invention is to provide an optical tomography system which can prevent deterioration of the image quality due to reduction in the measuring light or the reference light when the optical path length adjustment is effected.

In accordance with the present invention, there is provided an optical tomography system for obtaining a tomographic image of an object to be measured comprising a light source unit which emits light, a light dividing means which divides light emitted from the light source unit into measuring light and reference light, an optical path length adjusting means which adjusts an optical path length of the measuring light or the reference light which has been divided by the light dividing means, an optical fiber which guides the measuring light or the reference light to the optical path length adjusting means, a mixing means which mixes the reflected light from the object when the measuring light is projected onto the object and the reference light, an interference light detecting means which detects interference light of the reflected light and the reference light which have been mixed by the mixing means, and a tomographic image obtaining means which obtains a tomographic image of the object on the basis of the interference light detected by the interference light detecting means, wherein the improvement comprises that the optical path length adjusting means comprises a reflecting mirror which reflects the measuring light or the reference light radiated from the optical fiber, a first lens which is disposed between the reflecting mirror and the optical fiber to make parallel the measuring light or the reference light radiated from the core of the optical fiber and at the same time, to collect the measuring light or the reference light reflected by the reflecting mirror on the core of the optical fiber, and a second lens which collects the measuring light or the reference light made parallel by the first lens on the reflecting mirror and at the same time, makes parallel the measuring light or the reference light reflected by the reflecting mirror.

The optical path length adjusting means may further comprise a base portion to which the second lens and the reflecting mirror are fixed and a movement means which moves the base portion in the direction of the optical axis of the first lens.

Further, the optical path length adjusting means may further comprise a wedge-like transparent member disposed between the first and second lenses and a movement means which moves the transparent member in a direction perpendicular to the direction of the optical axis of the first lens.

Further, the optical path length adjusting means may further comprise an electro-optic element which is disposed between the first and second lenses and whose refractive index changes by applying an electric field and a drive power source which applies an electric field to the electro-optic element. The optical path length adjusting means may be a combination of the elements described above.

The light source unit may emit a laser beam while sweeping the wavelength, while the image obtaining means obtains a tomographic image of the object by carrying out frequency-analysis on the interference light, and the optical path length adjusting means changes the optical path length of the measuring light or the reference light so that a tomographic image signal can be obtained.

Further, the light source unit may emit low coherence light, while the image obtaining means obtains a tomographic image of the object by carrying out frequency-analysis on the interference light, and the optical path length adjusting means changes the optical path length of the measuring light or the reference light so that a tomographic image signal can be obtained.

Further, the light source unit may emit low coherence light, and the optical path length adjusting means may sweep the optical path length of the measuring light or the reference light in order to change the position in the direction of depth to be measured.

In accordance with the optical tomography system of the present invention, since the optical path length adjusting means comprises a reflecting mirror which reflects the measuring light or the reference light radiated from the optical fiber, a first lens which is disposed between the reflecting mirror and the optical fiber to make parallel the measuring light or the reference light radiated from the core of the optical fiber and at the same time, to collect the measuring light or the reference light reflected by the reflecting mirror on the core of the optical fiber, and a second lens which collects the measuring light or the reference light made parallel by the first lens on the reflecting mirror and at the same time, makes parallel the measuring light or the reference light reflected by the reflecting mirror, the focusing point of the first lens relatively to the core of the optical fiber and the focusing point of the second lens relatively to the reflecting mirror are kept unchanged when the optical path length of the measuring light or the reference light is adjusted between the first and second lenses, a tomographic image can be obtained from the interference light based on the stabilized amount of reference light and deterioration of the image quality is prevented.

When the optical path length adjusting means further comprises a base portion to which the second lens and the reflecting mirror are fixed and a movement means which moves the base portion in the direction of the optical axis of the first lens, since the focusing point of the first lens relatively to the core of the optical fiber and the focusing point of the second lens relatively to the reflecting mirror are kept unchanged when the optical path length of the measuring light or the reference light is adjusted, a tomographic image can be obtained from the interference light based on the stabilized amount of reference light and deterioration of the image quality is prevented.

When the optical path length adjusting means further comprises a wedge-like transparent member disposed between the first and second lenses and a movement means which moves the wedge-like transparent member in a direction perpendicular to the direction of the optical axis of the first lens, since the focusing point of the first lens relatively to the core of the optical fiber and the focusing point of the second lens relatively to the reflecting mirror are kept unchanged when the optical path length of the measuring light or the reference light is adjusted, a tomographic image can be obtained from the interference light based on the stabilized amount of reference light and deterioration of the image quality is prevented.

When the optical path length adjusting means further comprises, an electro-optic element which is disposed between the first and second lenses and whose refractive index changes by applying an electric field and a drive power source which applies an electric field to the electro-optic element since the focusing point of the first lens relatively to the core of the optical fiber and the focusing point of the second lens relatively to the reflecting mirror are kept unchanged when the optical path length of the measuring light or the reference light is adjusted, a tomographic image can be obtained from the interference light based on the stabilized amount of reference light and deterioration of the image quality is prevented.

Further, when the light source unit emits a laser beam while sweeping the wavelength, while the image obtaining means obtains a tomographic image of the object by carrying out frequency-analysis on the interference light, and the optical path length adjusting means changes the optical path length of the measuring light or the reference light so that a tomographic image signal can be obtained, a tomographic-image can be obtained from the interference light based on the stabilized amount of reference light and deterioration of the image quality is prevented.

Further, when the light source unit emits low coherence light, while the image obtaining means obtains a tomographic image of the object by carrying out frequency-analysis on the interference light, and the optical path length adjusting means changes the optical path length of the measuring light or the reference light so that a tomographic image signal can be obtained, a tomographic image can be obtained from the interference light based on the stabilized amount of reference light and deterioration of the image quality is prevented.

Further, when the light source unit emits low coherence light while and the optical path length adjusting means sweeps the optical path length of the measuring light or the reference light in order to change the position in the direction of depth to be measured, a tomographic image can be obtained from the interference light based on the stabilized amount of reference light and deterioration of the image quality is prevented.

BRIEF DESCRIPTION OF THE DRAWINGS

FIG. 7 is a schematic view showing another example of an optical path length adjusting means in the optical tomography system shown in FIG. 1, FIG. 8 is a schematic view showing sill another example of an optical path length adjusting means in the optical tomography system shown in FIG. 1, FIG. 9 is a schematic diagram showing an optical tomography system in accordance with a second embodiment of the present invention.

DESCRIPTION OF THE PREFERRED EMBODIMENTS

Figure 1:
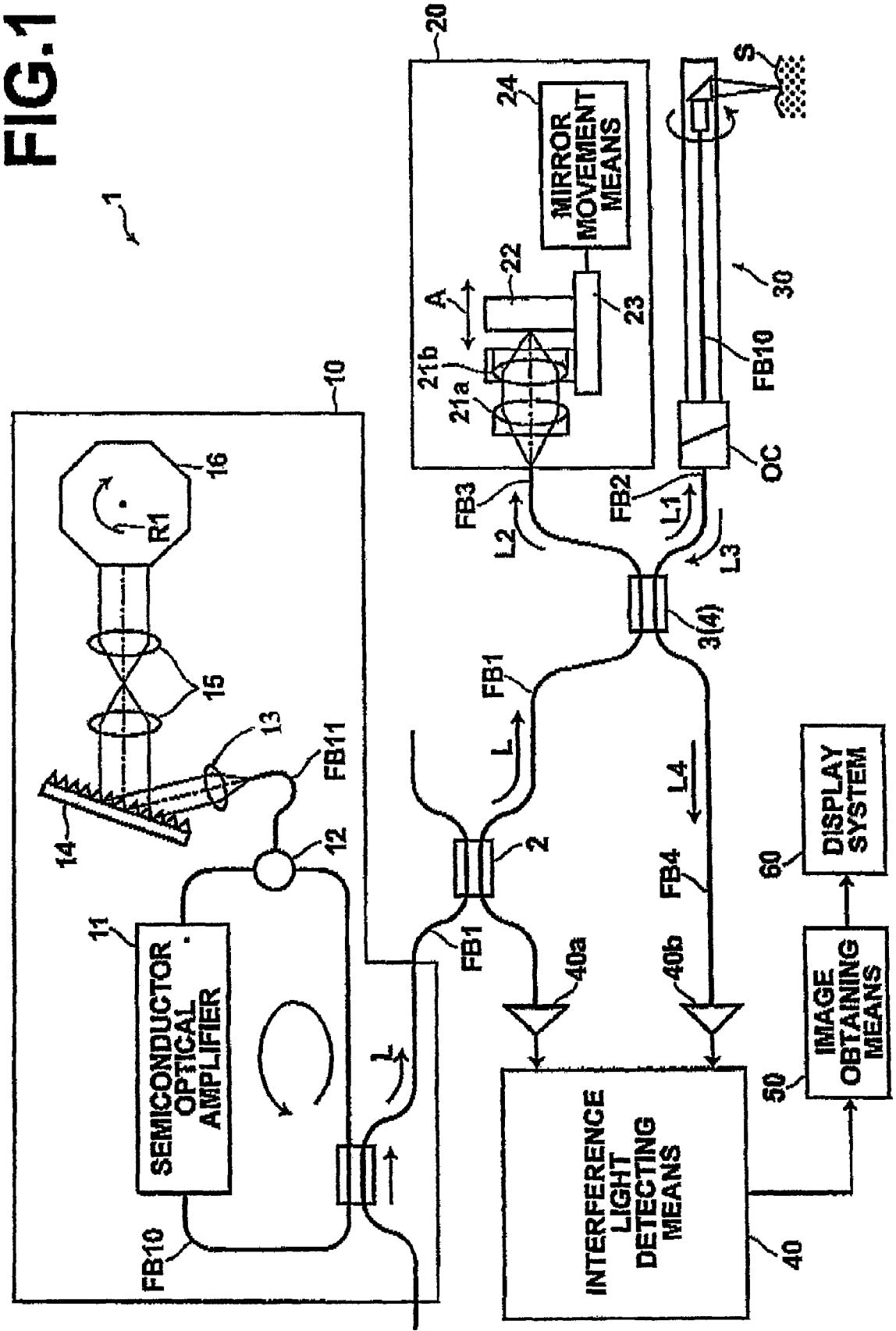
FIG. 1 is a schematic diagram showing an optical tomography system in accordance with a first embodiment of the present invention.

Embodiments of the present invention will be described in detail with reference to the drawings, hereinbelow. FIG. 1 is a schematic diagram that illustrates an optical tomography system in accordance with a first embodiment of the present invention. The optical tomography system 1 of this embodiment is for obtaining a tomographic image of an object of measurement such as a living tissue or a cell in a body cavity by measuring the SS-OCT. The optical tomography apparatus 1 of this embodiment comprises: a light source unit 10 for emitting a light beam L; a light dividing means 3 for dividing the light beam L emitted from the light source unit 10 into a measuring light beam L1 and a reference light beam L2; an optical path length adjusting means 20 for adjusting the optical path length of the reference light beam L2 divided by the light dividing means 3; a probe 30 which guides to the object S to be measured the measuring light beam L1 divided by the light dividing means 3; a mixing means 4 for mixing a reflected light beam L3 from the object S when the measuring light beam L1 is irradiated onto the object S, and the reference light beam L2; and an interference light detecting means 40 for detecting interference light beam L4 of the reflected light beam L3 and the reference light beam L2 which have been mixed.

The light source unit 10 emits the laser light beam L while sweeping the frequency at a constant period and comprises, for instance, a synchronized semiconductor laser. Specifically, the light source unit 10 comprises: a semiconductor optical amplifier 11 (semiconductor gain medium); and an optical fiber FB10 and the optical fiber FB10 is connected to both ends of the semiconductor optical amplifier 11. The semiconductor optical amplifier 11 functions to emit weak release light into a first end of the optical fiber FB10, when a drive current is injected thereinto, and to amplify the light that enters it from a second end of the optical fiber FB10. When the drive current is supplied to the semiconductor optical amplifier 11, a light beam L is emitted to an optical fiber FB1 from a resonator formed by the semiconductor optical amplifier 11 and the optical fiber FB10.

Further, an optical divider 12 is linked to the optical fiber FB10, and a portion of the light beam that propagates within the optical fiber FB10 is emitted into an optical fiber FB11. The light beam, which is emitted from the optical fiber FB11, passes through a collimating lens 13, a diffraction grating 14, and an optical system 15, to be reflected by a rotating polygon mirror 16. The light beam reflected by the rotating polygon mirror 16 passes through an optical system 15, the diffraction grating 14, and the collimating lens 13, to reenter the optical fiber FB11.

Figure 2:
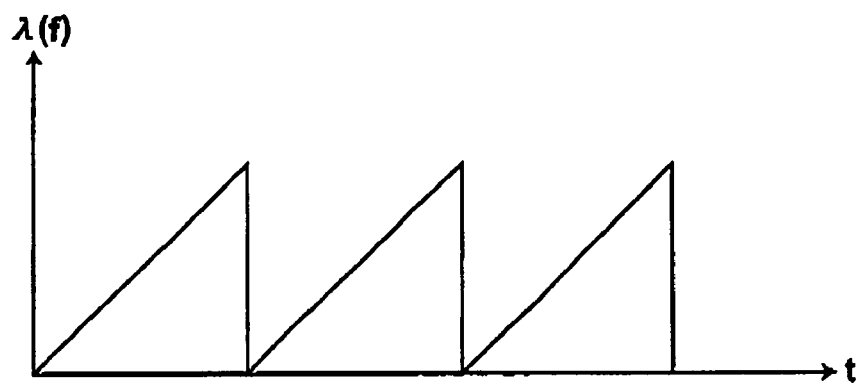
FIG. 2 is a view for illustrating the wavelength sweep of a laser beam output from the light source unit shown in FIG. 1.

The rotating polygon mirror 16 rotates in the direction indicated by arrow R1, to vary the angle of each reflective surface thereof with respect to the optical axis of the optical system 15. Thereby, only a light beam having a specific frequency, from among the light spectrally split by the diffraction grating 14, is returned to the optical fiber FB11. The frequency of the light beam that reenters the optical fiber FB11 is determined by the angle formed by the optical axis of the optical system 15 and the reflective surface of the rotating polygon mirror 16. The light beam of a specific frequency band that enters the optical fiber FB11 is caused to enter the optical fiber FB10 by the optical divider 12. As a result, the laser light beam L of the specific frequency is emitted toward the optical fiber FB1. Accordingly, when the rotating polygon mirror 16 rotates in the direction indicated by arrow R1 at a constant speed, the wavelength of the light beam which reenters the optical fiber FB11 is swept at a period as shown in FIG. 2. That is, a laser beam L which is swept in its wavelength at a period is emitted toward the optical fiber FB1.

The light dividing means 3 comprises, for instance, a 2×2 fiber optic coupler and divides the light beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In FIG. 1, the light dividing means 3 also functions as the mixing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

Figure 3:
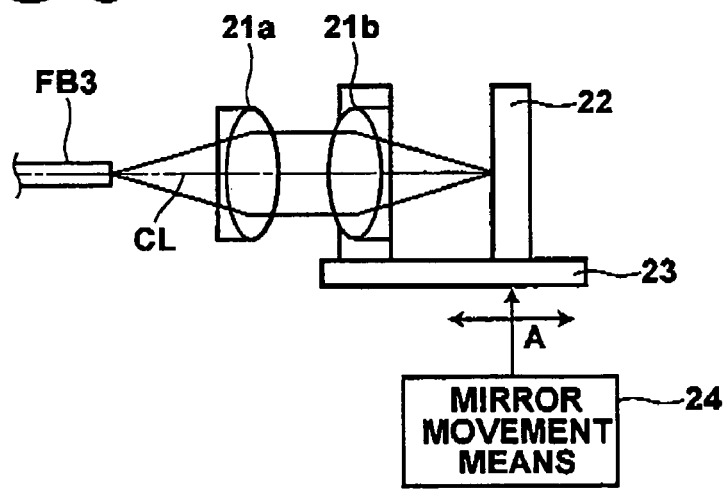
FIG. 3 is a schematic diagram showing an example of the optical path length adjusting means of an optical tomography system shown in FIG. 1, FIGS. 4A and 4B are views for illustrating the inclination of the reflecting mirror in the conventional optical path length adjusting mechanism.

The optical path length adjusting means 20 is disposed on the side of the optical fiber FB3 radiating the reference light beam L2. FIG. 3 is a schematic view showing an example of the optical path length adjusting means 20 and the optical path length adjusting means 20 will be described with reference to FIGS. 1 and 3. The optical path length adjusting means 20 changes the optical path length of the reference light beam L2 in order to adjust a range over which a tomographic image is to be obtained and comprises a reflecting mirror 22 which reflects the reference light beam L2 radiated from the optical fiber F3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 22 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22. That is, the first and second lenses 21a and 21b form a confocal optical system.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 20 is further provided with a base portion 23 to which the second lens 21b and the reflecting mirror 22 are fixed and a mirror movement means 24 which moves the base portion 23 in the direction of the optical axis of the first lens 21a. In response to movement of the base portion 23 in the direction of arrow A, the optical path length of the reference light beam L2 can be changed.

The mixing means 4 shown in FIG. 1 comprises a 2×2 fiber optic coupler as described-above, and mixes the reference light beam L2 which has been changed in its optical path length by the optical path length adjusting means 20 and the reflected light beam L3 from the object S to emit the mixed light beam toward the interference light detecting means 40 by way of an optical fiber FB4.

The interference light detecting means 40 detects interference light L4 of the reflected light beam L3 and the reference light beam L2 which have been mixed by the mixing means 4. The image obtaining means 50 obtains a tomographic image of the object S by carrying out frequency analysis on the signal of interference light beam L4 detected by the interference light detecting means 40. The obtained tomographic images are displayed by the display system 60. in the embodiment shown in FIG. 1, an optical detector 40a which detects the intensity of the laser light beam L branched from an fiber optic coupler 2 of the optical fiber FB1 and an optical detector 40b which detects the intensity of interference light beam L4 are provided and the interference light detecting means 40 has a function of adjusting the balance of the intensity of the interference light beam L4 on the basis of the output of the optical detector 40a. This function suppresses unevenness in the light intensity by the frequency and permits to obtain a clearer image.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When it is assumed that the light intensity of the interference fringes corresponding to each optical path length L when the reflected light beams L3 from depths of the object S and the reference light beam L2 interfere with each other with various optical path length differences is S(L), the light intensity I(k) detected in the interference light detecting means 40 is expressed by the following formula:

$$I(k) = \int_0^\infty S(L)[L + \cos(kL)]dL \qquad (1)$$

wherein k represents the wave number and L represents the optical path length difference. Formula (1) may be considered to be given as an interferogram of a frequency range having a wave number of ω/c (k=ω/c). Accordingly, a tomographic image is obtained by obtaining information on the distance of the object S from the measurement initiating position and information on the intensity of reflection by carrying out frequency analysis by Fourier-transform on the spectral interference fringes detected by the interference light detecting means 40 and determining the intensity S(L) of the interference light L4.

Operation of the optical tomography system 1 having a structure described above will be described with reference to FIGS. 1 to 3, hereinbelow. When a tomographic image is to be obtained, the optical path length is first adjusted by moving the base portion 23 in the direction of the arrow A so that the object S is positioned in the measurable area. The light beam L is emitted from the light source unit 10 by sweeping the wavelength at a period and the light beam L is divided into the measuring light beam L1 and the reference light beam L2 by the dividing means 3. The measuring light beam L1 is led by the optical probe 30 into a body cavity and is projected onto the object S. Then the reflected light beam L3 from the object S and the reference light beam L2 reflected by the reflecting mirror 22 are mixed, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50.

When the base portion 23 is moved in the direction of the arrow A in order to adjust the optical path length (FIG. 3), the focus of the first lens 21a is never moved from the core of the optical fiber FB3. Further, the focus of the second lens 21b is never moved from the reflecting mirror 22. Accordingly, reduction of the amount of the reference light beam L2 when the reference light beam reenters the optical fiber FB3 after adjusted with its optical path length can be prevented, whereby deterioration of the image quality due to change of the intensity of the interference light beam L4 every time the optical path length is adjusted can be prevented.

Figure 4A:
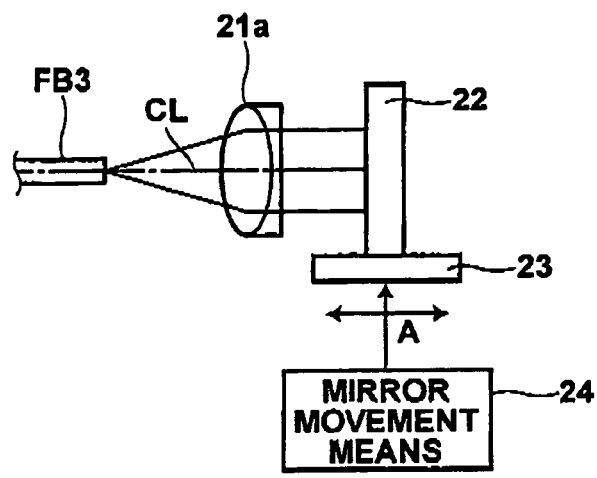
Figure 4B:
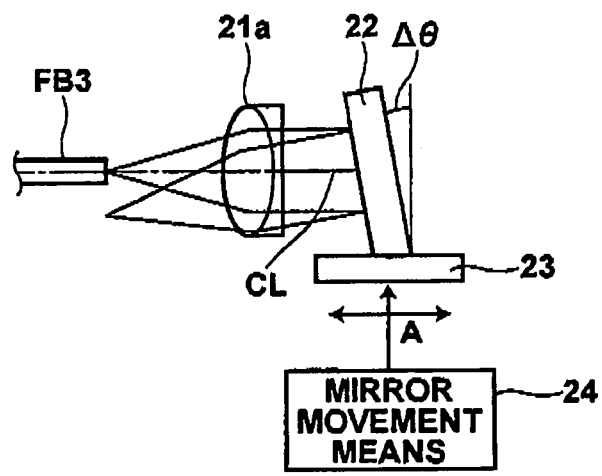
Figure 5:
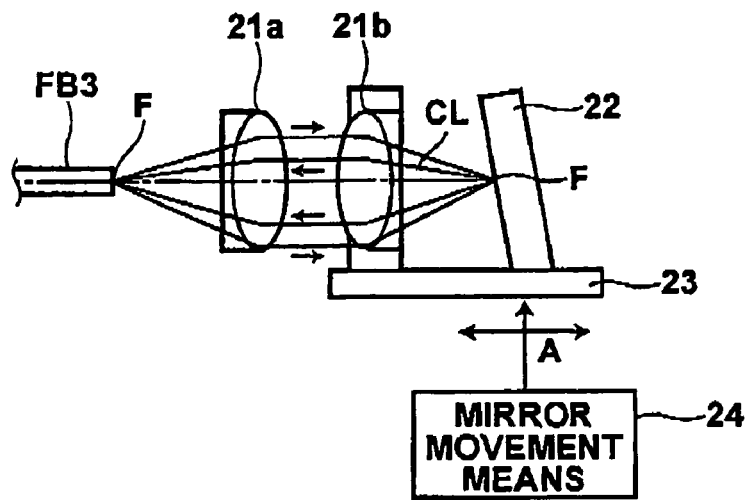
FIG. 5 is a view for illustrating the inclination of the reflecting mirror in the optical path length adjusting means shown in FIG. 3.

By forming a confocal optical system by the first and second lenses 21a and 21b, mounting errors may be increased when the second lens 21b and the reflecting mirror 22 are mounted on the base portion 23, whereby the optical path length adjusting means manufacturing efficiency can be improved. That is, it is necessary for the optical path length adjusting means 20 to cause the light radiated from the core of the optical fiber FB3 to reenter the core of the optical fiber FB3 which is several μm to ten μm in its diameter. When, in the conventional optical path length adjusting means shown in FIG. 4A, having a collimator lens 21a and a reflecting mirror 22, the reflecting mirror 22 is fixed to the base portion 23 inclined to the optical axis CL by Δθ as shown in FIG. 4B, the amount of the reference light L2 which enters the core of the optical fiber FB3 is reduced. Accordingly, in the conventional optical path length adjusting means shown in FIG. 4A, the reflecting face of the reflecting mirror 22 must be strictly perpendicular to the optical axis CL of the collimator lens 21a.

Figure 6:
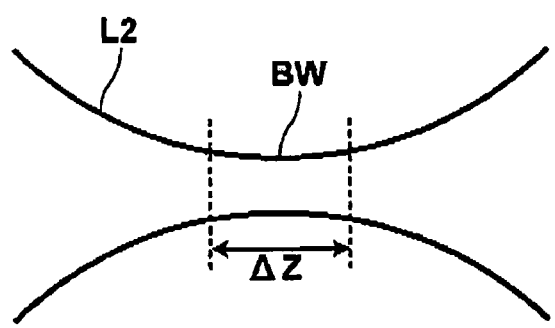
FIG. 6 is a view showing the beam waist formed in the focusing position of the second lens of FIG. 5.

Whereas, in the optical path length adjusting means 20 where the first and second lenses 21a and 21b form a confocal optical system, even if the reflecting mirror 22 is fixed to the base portion 23 inclined to the optical axis CL by Δθ, the reference light beam L2 reflected in the focusing position of the second lens 21b returns to the focusing position of the first lens 21a. Further, since the reference light beam L2 is a laser beam, a beam waist BW having a depth of focus of ΔZ is formed in the focusing position of the second lens 21b as shown in FIG. 6 and so long as the reflecting face of the reflecting mirror 22 is in the beam waist BW, the reference light beam L2 returns to the focusing position of the first lens 21a even if the reflecting mirror 22 is inclined by Δθ. Thus, the range of permissible mounting errors may be increased when the second lens 21b and the reflecting mirror 22 are mounted on the base portion 23, whereby the optical path length adjusting means manufacturing efficiency can be improved.

FIG. 7 is a schematic view showing the optical path length adjusting means in a tomography system of the present invention in accordance with a second embodiment. In the optical path length adjusting means 120 of FIG. 7, parts analogous to those shown in the optical path length adjusting means 20 of FIG. 3 are given the same reference numerals and will not be described here.

The optical path length adjusting means 120 further comprises a wedge-like transparent member 121 disposed between the first and second lenses 21a and 21b and a movement means 122 which moves the transparent member 121 in a direction perpendicular to the direction of the optical axis CL of the first lens 21a. In response to movement of the transparent member 121 in the direction of arrow B by the movement means 122, the optical path length of the reference light beam L2 is adjusted. It is preferred that the transparent member 121 be even in number. Also, in this case, reduction of the amount of the reference light beam L2 when the reference light beam L2 reenters the optical fiber FB3 after adjusted with its optical path length by the optical path length adjusting means 120 can be prevented, whereby deterioration of the image quality due to change of the intensity of the interference light beam L4 every time the optical path length is adjusted can be prevented.

FIG. 8 is a schematic view showing the optical path length adjusting means in a tomography system of the present invention in accordance with a third embodiment. In the optical path length adjusting means 220 of FIG. 8, parts analogous to those shown in the optical path length adjusting means 20 of FIG. 3 are given the same reference numerals and will not be described here.

The optical path length adjusting means 220 of FIG. 8 further comprises an electro-optic element 221 which is disposed between the first and second lenses 21a and 21b and whose refractive index changes by applying an electric field and a drive power source 222 which applies an electric field to the electro-optic element 221. In response to application of an electric field to the electro-optic element 221 by the drive power source 222, the refractive index of the electro-optic element 221 changes according to the intensity of the electric field, and the optical path length of the reference light beam L2 is adjusted. Also, in this case, reduction of the amount of the reference light beam L2 when the reference light beam L2 reenters the optical fiber FB3 after adjusted with its optical path length by the optical path length adjusting means 220 can be prevented, whereby deterioration of the image quality due to change of the intensity of the interference light beam L4 every time the optical path length is adjusted can be prevented.

FIG. 9 is a schematic view showing a tomography system of the present invention in accordance with another embodiment. The tomography system 100 will be described with reference to FIG. 9. In the tomography system 100 of FIG. 9, parts analogous to those shown in the tomography system 1 of FIG. 1 are given the same reference numerals and will not be described here. The tomography system 100 of FIG. 9 differs from the tomography system 1 of FIG. 1 in the light source unit and the interference light detecting means. Specifically, the tomography system 100 is for obtaining a tomographic image of an object in a body cavity by measuring the SD-OCT and the light source unit 110 comprises a light source 111 emitting low coherence light such as an SLD (super luminescent diode) or an ASE (amplified spontaneous emission) and an optical system 112 which causes the light beam emitted from the light source 111 to enter an optical fiber FB1. Since the optical tomography system 1 of this embodiment is for obtaining a tomographic image with a part of a living tissue in a body cavity taken as the object S, it is preferred that the light source 111 be, for instance, a broad spectral band, ultra short pulse laser where attenuation of light due to scatter and/or absorption when transmitted through the object S is minimized.

The interference light detecting means 140 detects interference light L4 of the reflected light beam L3 and the reference light beam L2 which have been mixed by the mixing means 4, and comprises a spectral means 142 which divides the interference light beam L4 having a plurality of wavelength bands by the wavelength bands and a light detecting means 144 which detects the amount of light of each wavelength band of the interference light beam L4 divided by the spectral means 142. The spectral means 142 comprises, for instance, a diffraction grating element, and divides the interference light beam L4 entering it by way of the collimator lens 141 to output the divided interference light beam L4 to the light detecting means 144.

The light detecting means 144 is formed by a plurality of photo sensors which comprises a plurality of, for instance, one-dimensionally or two-dimensionally arranged CCDs and each of the photo sensors detects each wavelength band of the interference light beam L4 entering by way of an optical system 143. Information on the intensity of the reflected light beam of the positions in the direction of depth is obtained by carrying out frequency analysis in the image obtaining means 50 on a signal of the interference light beam L4 detected in the interference light detecting means 144, and an optical tomographic image can be generated.

Also, in the optical tomography system 100 of FIG. 9, reduction of the amount of the reference light beam L2 when the reference light beam L2 reenters the optical fiber FB3 after adjusted with its optical path length by the optical path length adjusting means 20 can be prevented, whereby deterioration of the image quality due to change of the intensity of the interference light beam L4 every time the optical path length is adjusted can be prevented.

Figure 10:
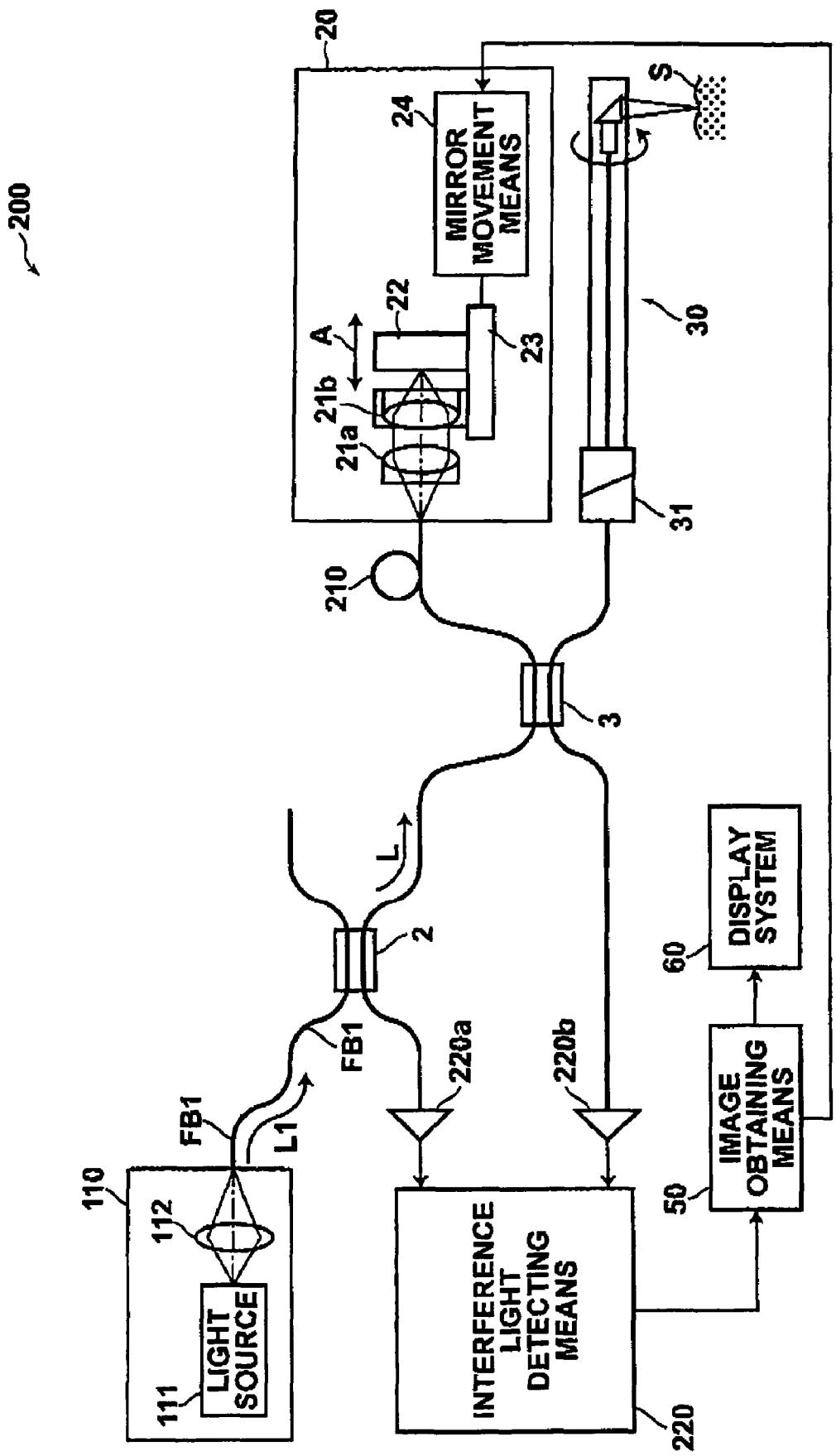
FIG. 10 is a schematic diagram showing an optical tomography system in accordance with a third embodiment of the present invention.

FIG. 10 is a schematic view showing a tomography system of the present invention in accordance with still another embodiment. The tomography system 200 will be described with reference to FIG. 10. In the tomography system 200 of FIG. 10, parts analogous to those shown in the tomography system 1 of FIG. 1 and the tomography system 100 of FIG. 9 are given the same reference numerals and will not be described here.

The tomography system 200 is for obtaining a tomographic image of an object in a body cavity by measuring the so-called TD-OCT and the optical path length adjusting means 20 has a function of changing the optical path length of the reference light beam L2, thereby changing the measuring position in the object S in the direction of depth. On the optical path of the reference light beam L2 (the optical fiber FB3), a phase modulator 210 is disposed and the phase modulator 210 has a function of giving a slight frequency shift to the reference light beam L2. The reference light beam L2 is guided to the optical fiber FB4 by way of the mixing means 4 after adjusted with its optical path length and frequency-shifted by the optical path length adjusting means 20.

The interference light detecting means 220 detects the interference light beam L4 by, for instance, heterodyne detection. Specifically, when the whole optical path length which the measuring light beam L1 travels back and forth from the dividing means 3 to the reflecting point in the object S is substantially equal to the whole optical path length which the reference light beam L2 travels back and forth from the dividing means 3 and the reflecting mirror 22, a beat signal which varies in intensity at the modulating frequency of the phase modulator 210 is generated. As the optical path length is changed by the optical path length adjusting means 20, the measuring position (the depth of measurement) in the object S changes and the interference light detecting means 220 detects the beat signal in each measuring position. Information on the measuring positions is output to the image obtaining means from the optical path length adjusting means 20. Then a tomographic image is generated on the basis of the beat signal detected by the interference light detecting means 220 and information on the moving distance from the mirror movement means 24.

Also, in the optical tomography system 200 where TD-OCT is measured, reduction of the amount of the reference light beam L2 when the reference light beam L2 reenters the optical fiber FB3 after adjusted with its optical path length by the optical path length adjusting means 20 can be prevented, whereby deterioration of the image quality due to change of the intensity of the interference light beam L4 every time the optical path length is adjusted can be prevented.

In accordance with each embodiment described above, since the optical path length adjusting means comprises first and second lenses 21a and 21b forming a confocal optical system, the focusing point of the first lens 21a relatively to the core of the optical fiber FB3 and the focusing point of the second lens 21b relatively to the reflecting mirror 22 are kept unchanged when the optical path length of the measuring light beam L1 or the reference light beam L2 is adjusted between the first and second lenses 21a and 21b, a tomographic image can be obtained from the interference light based on the stabilized amount of reference light L2 and deterioration of the image quality can be prevented.

When the optical path length adjusting means 120 further comprises a wedge-like transparent member 121 disposed between the first and second lenses 21a and 21b and a movement means 122 which moves the wedge-like transparent member 121 in a direction perpendicular to the direction of the optical axis of the first lens 21a as shown in FIG. 7, since the focusing point of the first lens 21a relatively to the core of the optical fiber and the focusing point of the second lens 21b relatively to the reflecting mirror 22 are kept unchanged when the optical path length of the measuring light or the reference light is adjusted, a tomographic image can be obtained from the interference light based on the stabilized amount of reference light beam L2 and deterioration of the image quality is prevented.

When the optical path length adjusting means 220 further comprises, an electro-optic element 221 which is disposed between the first and second lenses 21a and 21b and whose refractive index changes by applying an electric field and a drive power source 222 which applies an electric field to the electro-optic element 221 as shown in FIG. 8, since the focusing point of the first lens 21a relatively to the core of the optical fiber and the focusing point of the second lens 21b relatively to the reflecting mirror are kept unchanged when the optical path length is adjusted, a tomographic image can be obtained from the interference light based on the stabilized amount of reference light L2 and deterioration of the image quality is prevented.

When the optical path length adjusting means 120 further comprises, an electro-optic element 221 which is disposed between the first and second lenses 21a and 21b and whose refractive index changes by applying an electric field and a drive power source 222 which applies an electric field to the electro-optic element 221 as shown in FIG. 8, since the focusing point of the first lens 21a relatively to the core of the optical fiber and the focusing point of the second lens 21b relatively to the reflecting mirror are kept unchanged when the optical path length is adjusted, a tomographic image can be obtained from the interference light based on the stabilized amount of reference light L2 and deterioration of the image quality is prevented.

The optical path length adjusting means 20, 120 and 220 described above may be applied to any one of the optical tomography system 1 shown in FIG. 1 where SS-OCT is measured, the optical tomography system 100 shown in FIG. 9 where SS-OCT is measured, and the optical tomography system 200 shown in FIG. 10 where SS-OCT is measured. The optical path length adjusting means may be in the form of a composite of these optical path length adjusting means 20, 120 and 220.

This invention need not be limited to the embodiments described above. Though, in FIG. 1, the optical path length adjusting means 20 adjusts the optical path length of the reference light beam L2 by way of example, it may adjust the optical path length of the measuring light beam L1. In this case, for instance, a three-way optical circulator is provided in the optical fiber FB2 which guides the measuring light beam L1 in FIG. 1, and the optical path length adjusting means 20 described above is in the port which is not in operation. Then by leading returning light from the object S to the optical path length adjusting means 20 and by returning the reflected light beam from the reflected mirror 22 at the end of the optical path length adjusting means 20 to the mixing means 4, similar result can be obtained. Further, though, in the optical tomography systems 100 and 200 shown in FIGS. 9 and 10, the optical path length adjusting means 20 shown in FIG. 3 is employed, by way of example, the optical path length adjusting means 120 and 220 shown in FIGS. 7 and 8 may be employed.

What is claimed is:

1. An optical tomography system for obtaining a tomographic image of an object to be measured, the system comprising:
   a light source unit which emits light,
   a light dividing means for dividing light emitted from the light source unit into measuring light and reference light,
   an optical path length adjusting portion which adjusts an optical path length of the measuring light or the reference light which has been divided by the light dividing means,
   an optical fiber which guides the measuring light or the reference light to the optical path length adjusting portion,
   a mixing means for mixing light reflected from the object when the measuring light is projected onto the object and the reference light,
   an interference light detecting means for detecting interference light of the reflected light and the reference light which have been mixed by the mixing means, and
   a tomographic image obtaining means for obtaining a tomographic image of the object by carrying out a frequency analysis on the interference light detected by the interference light detecting means,
   wherein the optical path length adjusting portion comprises:
   a reflecting mirror which reflects the measuring light or the reference light radiated from the optical fiber,
   a first lens which is disposed between the reflecting mirror and the optical fiber to make parallel the measuring light or the reference light radiated from the core of the optical fiber and at the same time, to collect the measuring light or the reference light reflected by the reflecting mirror on the core of the optical fiber, and
   a second lens which focuses the measuring light or the reference light made parallel by the first lens on the reflecting mirror and at the same time, makes parallel the measuring light or the reference light reflected by the reflecting mirror.

2. The optical tomography system as defined in claim 1, wherein the optical path length adjusting portion further comprises:
   a base portion to which the second lens and the reflecting mirror are fixed; and
   a movement means which moves the base portion in the direction of the optical axis of the first lens.

3. The optical tomography system as defined in claim 1, wherein the optical path length adjusting portion further comprises:
   a wedge-like transparent member disposed between the first and second lenses; and
   a movement means for moving the transparent member in a direction perpendicular to the direction of the optical axis of the first lens.

4. The optical tomography system as defined in claim 1, wherein the optical path length adjusting portion further comprises:
   an electro-optic element which is disposed between the first and second lenses and whose refractive index changes by applying an electric field; and
   a drive power source which applies an electric field to the electro-optic element.

5. The optical tomography system as defined in claim 1, wherein:
   the light source unit emits a laser beam while sweeping the wavelength at a constant period, and
   the optical path length adjusting portion changes the optical path length of the measuring light or the reference light to obtain a tomographic image signal.

6. The optical tomography system as defined in claim 1, wherein:
   the light source unit emits low coherence light, and
   the optical path length adjusting portion changes the optical path length of the measuring light or the reference light to obtain a tomographic image signal.

7. The optical tomography system as defined in claim 1, wherein:
   the light source unit emits low coherence light, and
   the optical path length adjusting portion sweeps the optical path length of the measuring light or the reference light to change the position in the direction of depth to be measured.

8. The optical tomography system as defined in claim 1, wherein the light from the light source, the reference light, and the measuring light each comprises a broad band, low coherence light.

9. An optical path length adjusting apparatus for adjusting a measuring light or reference light in an optical tomography system for obtaining an optical coherence tomographic image of an object to be measured, wherein the optical tomography system carries the measuring light or reference light on an optical fiber, the optical path length adjusting apparatus comprising:
   a first lens that collimates the reference or measuring light from the optical fiber;
   a mirror for reflecting the light;
   a second lens that focuses the collimated light from the first lens onto the mirror, and collimates light reflected by the mirror;
   an optical path length changing apparatus; and
   a base portion to which the second lens and the reflecting mirror are fixed.

10. The optical path length adjusting apparatus as defined in claim 9, wherein the optical path length changing apparatus comprises means for changing the length of the optical path length.

11. The optical path length adjusting apparatus as defined in claim 9, wherein the optical path length changing apparatus comprises a mechanical stage, movable along the direction of the optical axis, on which the second lens and the mirror are mounted.

12. The optical path length adjusting apparatus as defined in claim 9, wherein the optical path length changing apparatus comprises a material whose index of refraction is changeable.

13. The optical path length adjusting apparatus as defined in claim 9, wherein the optical path length changing apparatus comprises an optical wedge.

* * * * *